United States Patent [19]

Olmo

[11] Plant 4,856

[45] Jun. 8, 1982

[54] GRAPEVINE

[75] Inventor: Harold P. Olmo, Davis, Calif.

[73] Assignee: The Regents of the University of California, Berkeley, Calif.

[21] Appl. No.: 189,538

[22] Filed: Sep. 22, 1980

[51] Int. Cl.[3] ..... A01H 5/00

[52] U.S. Cl. ..... Plt./47

[58] Field of Search ..... Plt./47

*Primary Examiner*—James R. Feyrer

*Attorney, Agent, or Firm*—Townsend & Townsend

[57] ABSTRACT

A new and distinct variety of grapevine of the vinifera species having the general characteristics of the commercial Emperor but differing in the following important attributes: Earlier coloring and maturity of the fruit, a much brighter red color, essentially seedless with only soft greenish rudiments present, and similar to Emperor in shipping and cold storage qualities.

4 Drawing Figures

This invention relates to a new and distinct variety of grapevine of the vinifera species, having the general characteristics of the commercial Emperor, but differing in the following important attributes: earlier in coloring and maturity of the fruit, a much brighter red color, essentially seedless (only soft greenish rudiments present). Shipping and cold storage tests of the fruit have given results similar to Emperor.

The new variety, 31-37F, is the result of crossing Emperor with the California selection Z4-87.

Parentage:

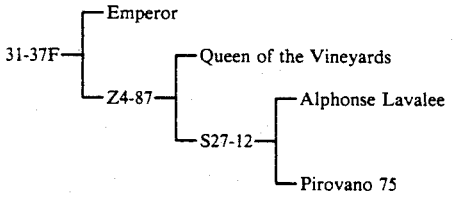

The cross was made at the University Vineyard at Davis in May 1966, and the young seedling vines were transplanted at the Kearney Horticultural Field Station July 6, 1967. The first crop was harvested July 7, 1970, at which time the vine was noted for the heavy crop of fruit, with bright red, seedless berries of large size.

The new variety was asexually reproduced at the Kearney Horticultural Field Station by Yema budding (grafting) six vines to the rootstock Ganzin 1 on Sept. 9, 1970, using buds (eyes) taken from the original vine. This propagation provided better observation of the variety with growth under standard spacing and cultural treatments approximating commercial conditions. These vines fruited in 1972 and were observed seasonally since that time. The vine and fruit characteristics remained essentially identical to the original vine.

Only the color of the berry referred to in the following description under the heading "Plant Characteristics" is considered a distinctive feature of the plant of this invention and has been identified according to Nickersons Color Fan, Munsell Color Co., Baltimore, Md. Other colors are not considered distinctive or diagnostic of the plant variety and for this reason have not been positively identified.

PLANT CHARACTERISTICS

Vine: Vigorous, with growth habit similar to Emperor, but with more numerous and slenderer canes, trunk straight with loose and abundant bark, bud burst late, with or slightly before Emperor; first blossoms on May 17 at Parlier, Calif.; highly fruitful; basal buds more fertile than Emperor; adapted to short spur pruning on bilateral cordon; leaf fall late, shows foliage symptoms of magnesium deficiency when heavily cropped.

Figure 1:
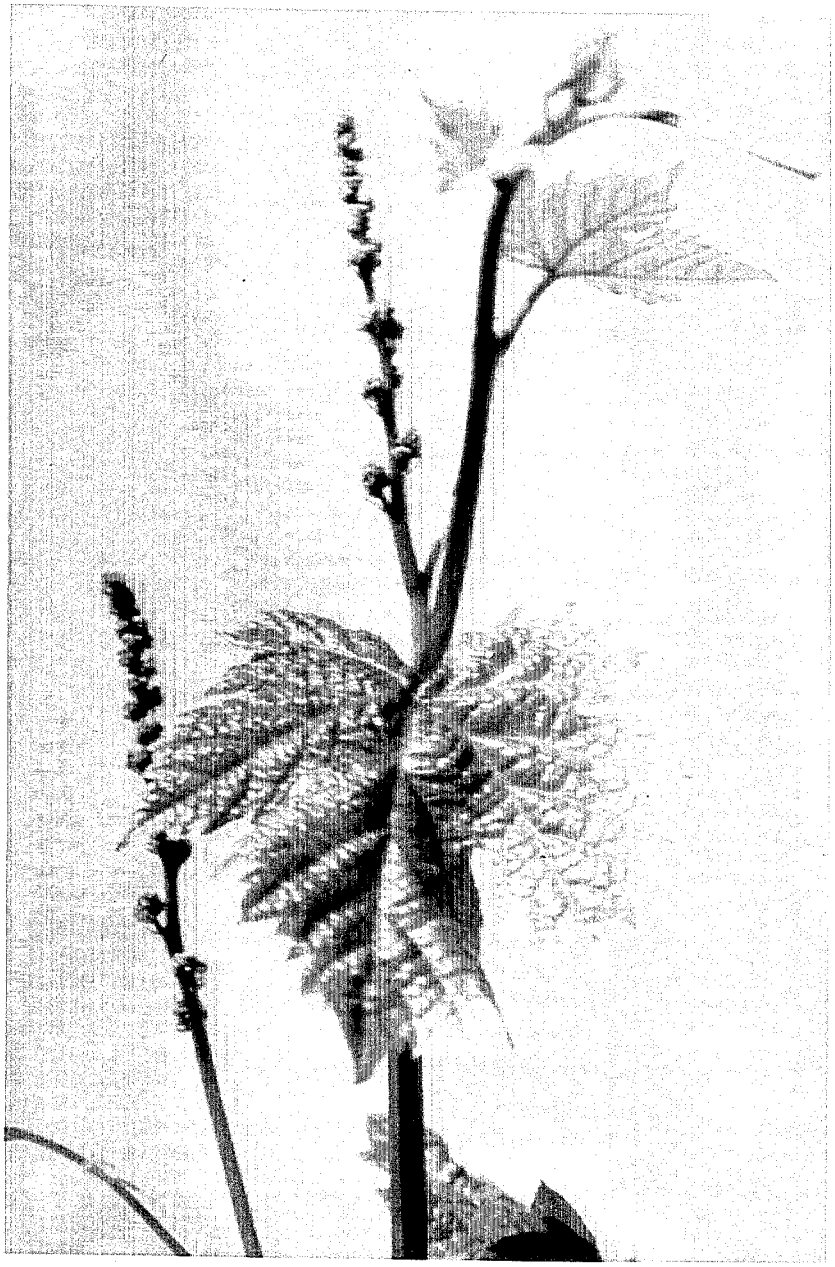
FIG. 1 illustrates a typical shoot tip of the new grape variety.

Shoot tip: (12"–14" long) (see FIG. 1) straight, very slender, youngest leaves white wooly above and below, teeth edged carmine; half-expanded leaf with loose, scattered hairs, not flocculent; blade very undulated, lobes folded inward, petioles and shoot maroon on sun-exposed portions, ribbed; inflorescence very narrow and linear.

Shoot: Strongly attached; flattened, especially at nodes, with maroon striations.

Figure 2:
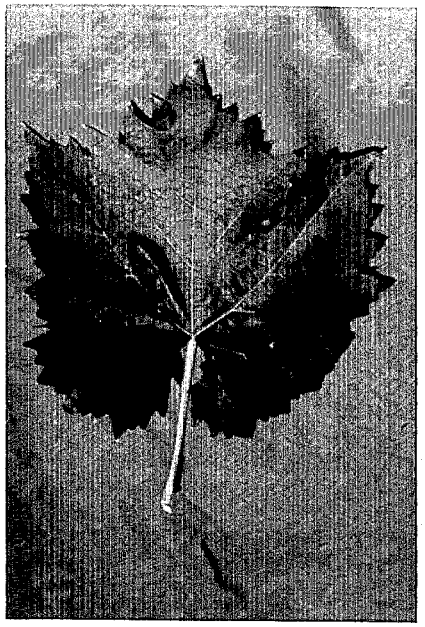
FIG. 2 illustrates the lower surface of a leaf typical of the new grape variety.
Figure 3:
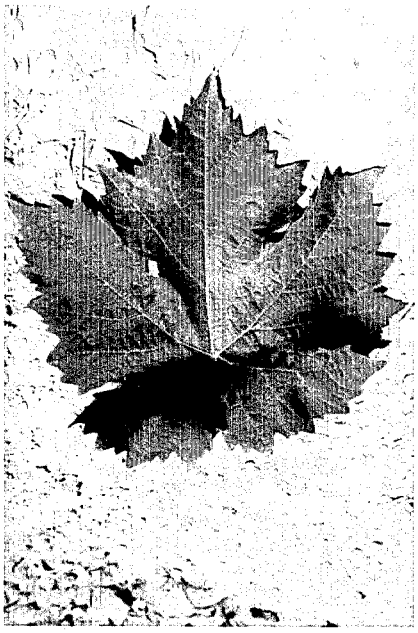
FIG. 3 illustrates the upper surface of a leaf typical of the new grape variety.
Figure 4:
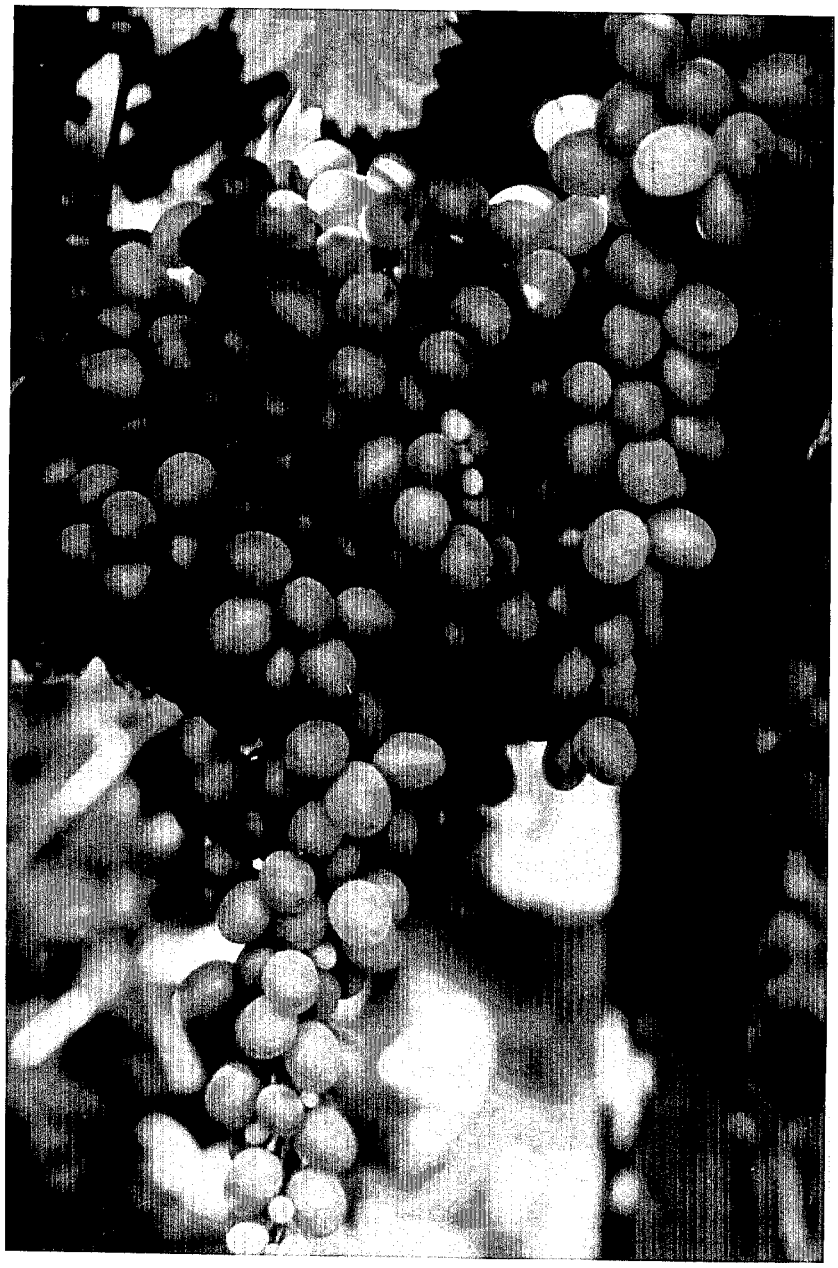
FIG. 4 illustrates a typical cluster of the new variety.

Leaf: (see FIG. 2) large, blade 18.5×19.6 cm., almost entire, with floccose wooly hairs on under surface, superior sinuses reduced to slits, shallow, overlapping and completely closed; teeth large, acute, with very straight sides; petiolar sinus deep, open, lyre-shaped; petiole slender, length 9.5 cm.

Cluster: The primary cluster is large, well-filled to compact, 12×36 cm., uniformly long conical and symmetrical, average 450 gm., the main rachis bearing an average of 250 berries, a long tendril branch occasionally forming a loose wing of 10 to 30 berries. Cluster stem 6 mm. diameter, woody and brown to first right angle bend at 3.4 cm. from point of attachment to cane, thence another 3.4 cm. to the beginning of lateral branching. Cluster usually borne freely pendant at fourth node, less frequently clusters at both fourth and fifth nodes; well-filled to compact, few small persistent green (immature) shot berries sometimes at apical end of cluster.

Berry: Ovoid, 10 largest per cluster average 3.8 gm., with tender skin and meaty flesh, deep pink when fully mature (2.5 R 6/11, Nickerson's Color Fan, Munsell Color Co.), without the purplish cast and thus more attractive than Emperor, seeds partly developed but green and fleshy; pedicels slender, warty, 9–10 mm. long, torus small.

At Parlier, Calif., first coloring (veraison) of the ripening fruit is approximately July 25 and is fully colored by August 20. Leaf removal and cane positioning are recommended to obtain more light and better coloring.

The fruit is retained in good condition on the vine for a long period. Fruit is suitable for cold storage.

This new variety should succeed best in sites where the Emperor has been successful. It most resembles the variety Ruby Seedless (unpatented) but is later maturing and has brighter red color.

I claim:

1. The new and distinct grapevine herein described and illustrated, and identified by the characteristics enumerated above.

* * * * *